US008825680B2

(12) United States Patent
Burke et al.

(10) Patent No.: US 8,825,680 B2
(45) Date of Patent: Sep. 2, 2014

(54) METHOD AND APPARATUS FOR DISPLAYING NON-STANDARD-COMPLIANT IMAGES

(75) Inventors: Glenn Burke, Cleveland, OH (US); Gary Keefe, Brecksville, OH (US); Lawrence Srnka, Northfield Center, OH (US); Peter Botten, Lakewood, OH (US)

(73) Assignee: Codonics, Inc., Middleburg Heights, OH (US)

( * ) Notice: Subject to any disclaimer, the term of this patent is extended or adjusted under 35 U.S.C. 154(b) by 103 days.

(21) Appl. No.: 13/270,156

(22) Filed: Oct. 10, 2011

(65) Prior Publication Data

US 2012/0179670 A1 Jul. 12, 2012

Related U.S. Application Data

(60) Provisional application No. 61/391,632, filed on Oct. 9, 2010.

(51) Int. Cl.
*G06F 17/30* (2006.01)
(52) U.S. Cl.
USPC ....................................... 707/756
(58) Field of Classification Search
CPC ..... G06F 19/321; G06F 19/322; G06F 19/00; G06F 17/30; H04N 7/01
USPC ................. 707/783, 999.103, 665, 667, 756; 386/225, 323; 348/443
See application file for complete search history.

(56) References Cited

U.S. PATENT DOCUMENTS 6,260,021 B1 * 7/2001 Wong et al. ............ 707/999.103
2002/0019751 A1 * 2/2002 Rothschild et al. ............... 705/3
2002/0048222 A1 * 4/2002 Wright et al. ..................... 369/1

* cited by examiner

*Primary Examiner* — Vincent F Boccio
(74) *Attorney, Agent, or Firm* — Pearne & Gordon LLP

(57) ABSTRACT

Provided is a method of converting a medical image used in a network at a patient care facility, the network including an enterprise network storage solution optionally dedicated for storing medical images in a standardized medical imaging format that are to be retrieved over the network. The method includes us a computer system to search a portable computer-readable medium for an indication that the medical image is stored in a proprietary format on the portable computer-readable medium. The proprietary format of the medical image is identified, using the computer system, based on the indication. The medical image is converted into a format that is compliant with a standardized medical-imaging format, transmitted in the standardized medical-imaging format to be: (i) subsequently displayed by a display device without requiring prior storage of the medical image in an enterprise storage solution for medical images, and/or (ii) stored in the enterprise storage solution.

11 Claims, 6 Drawing Sheets

METHOD AND APPARATUS FOR DISPLAYING NON-STANDARD-COMPLIANT IMAGES

CROSS-REFERENCE TO RELATED APPLICATIONS

This application claims the benefit of U.S. Provisional Application No. 61/391,632, filed Oct. 9, 2010, which is incorporated in its entirety herein by reference.

BACKGROUND OF THE INVENTION

1. Field of the Invention

This application relates generally to viewing medical images and, more specifically, to a method and apparatus for locally retrieving a medical image stored in a proprietary format and converting that medical image into an image that is compliant with a medical imaging standard.

2. Description of Related Art

During a surgical or other medical procedure the treating physician will often wish to review medical images taken of the patient. For instance, a physician may wish to view an x-ray or ultrasound of the patient on a video monitor hanging in the operating room while performing a surgical procedure. The x-ray or ultrasound images may show the medical condition of the patient being addressed during the surgical procedure, may show neighboring organs that the physician must avoid during the surgical procedure, or any other medical images of interest to a physician conducting a surgical procedure. However, in some cases the medical images the physician may wish to view are stored in a proprietary format on a CD, DVD, portable USB drive, or other portable computer-readable medium.

Conventionally, to view medical images stored on a portable computer-readable medium in an operating room, the CD or other medium is taken to a radiology workstation at a remote location from the operating room. The CD is loaded into the radiology workstation and the proprietary medical images are viewed from the CD using a proprietary viewer and exported in a standard medical image format. In order for the medical images to be preserved with the highest possible quality, and to facilitate standardized storage of medical images, the medical images are stored in a picture archiving and communication system ("PACS") in a Digital Imaging and Communications in Medicine ("DICOM") format. Once the medical images are stored in the PACS, they can be retrieved over a local network from the PACS to be displayed on the video monitor in the operating room.

However, if there are several medical images stored on the CD, a significant amount of time is required for the user of the radiology workstation to individually select each medical image from the CD, export them into the DICOM format, and then store those converted medical images in the PACS. Such a method of exporting the medical images using a specially-programmed workstation at a remote location before being able to view the medical images in the operating room is complex and time consuming. And due to the many different proprietary viewers required for viewing and exporting proprietary medical images stored on the CD, the user of the radiology workstation is required to have at least a minimal amount of familiarity with each.

BRIEF SUMMARY

Accordingly, there is a need in the art for a method and apparatus for locally converting medical images from a proprietary format into a format allowing local viewing of the medical images without requiring the medical images to first be stored in a PACS. The converted medical images are to be of sufficient quality for use in a medical application, and can optionally be compliant with a medical imaging standard.

According to one aspect, the subject application involves a method of converting a medical image used in a network at a patient care facility, the network including an enterprise network storage solution optionally dedicated for storing medical images in a standardized medical imaging format that are to be retrieved over the network. The method includes us a computer system to search a portable computer-readable medium for an indication that the medical image is stored in a proprietary format on the portable computer-readable medium. The proprietary format of the medical image is identified, using the computer system, based on the indication. The medical image is converted into a format that is compliant with a standardized medical-imaging format, transmitted in the standardized medical-imaging format to be: (i) subsequently displayed by a display device without requiring prior storage of the medical image in an enterprise storage solution for medical images, and/or (ii) stored in the enterprise storage solution.

According to another aspect, converting the medical image includes exporting, with a medical image export utility executing on the computer system, the medical image from the portable computer-readable medium into a non-proprietary format in response to identifying the proprietary format of the medical image. The medical image is stored, at least temporarily, in the non-proprietary format in a computer-accessible memory operatively connected to the computer system. The method also includes converting the medical image in the non-proprietary format to the format that is compliant with the standardized medical-imaging format.

According to another aspect, the subject application involves a computer terminal that is locally connected to a display device to display a medical image on the display device. The computer terminal includes a non-transitory computer readable memory storing computer-executable instructions that, when executed, cause the computer to perform a method. The method includes initiating a search of a portable computer-readable medium provided to the computer terminal for an indication of a proprietary format of the medical image. In response to detecting the proprietary format of the medical image, a medical image export utility stored on the portable computer-readable medium is executed and, using the medical image export utility, the medical image is stored in a non-proprietary format on a computer memory that is accessible to the local computer. The medical image is converted from the non-proprietary format to a DICOM-compliant format on the computer memory, and then displayed in the DICOM-compliant format with a display device without requiring prior storage of the medical image in a PACS storage server.

According to another aspect, the subject application involves a patient care facility where a patient is to receive medical attention. The patient care facility includes at least one medical modality for capturing a medical image associated with the patient, a display device for viewing the medical image, and a computer terminal in communication with the display device to display a medical image on the display device. The computer terminal includes a non-transitory computer readable memory storing computer-executable instructions that, when executed, cause the computer terminal to perform a method. The method includes initiating a search of a portable computer-readable medium in local communication with the computer terminal for an indication of a proprietary format of the medical image. In response to detecting the proprietary format of the medical image, a medical image export utility stored on the portable computer-readable medium is executed for exporting the medical image in the proprietary format from the portable computer-readable medium to be saved in a computer memory accessible to the computer terminal. Using the medical image export utility, the medical image is stored in a non-proprietary format on the computer memory. The medical image is converted from the non-proprietary format to a format that is compliant with a medical imaging standard, and displayed by a display device without requiring prior storage of the medical image in an enterprise storage solution for medical images.

According to another aspect, the subject application involves a method of converting a medical image to be displayed. The method includes initiating a search of a portable computer-readable medium for an indication of a format of the medical image. The method also includes establishing that the medical image is stored on the portable computer-readable medium in a non-proprietary format. The medical image is converted from the non-proprietary format to a format that is compliant with a medical imaging standard, and displaying with a display device without requiring prior storage of the medical image in an enterprise storage solution for medical images.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

DETAILED DESCRIPTION

Figure 1:
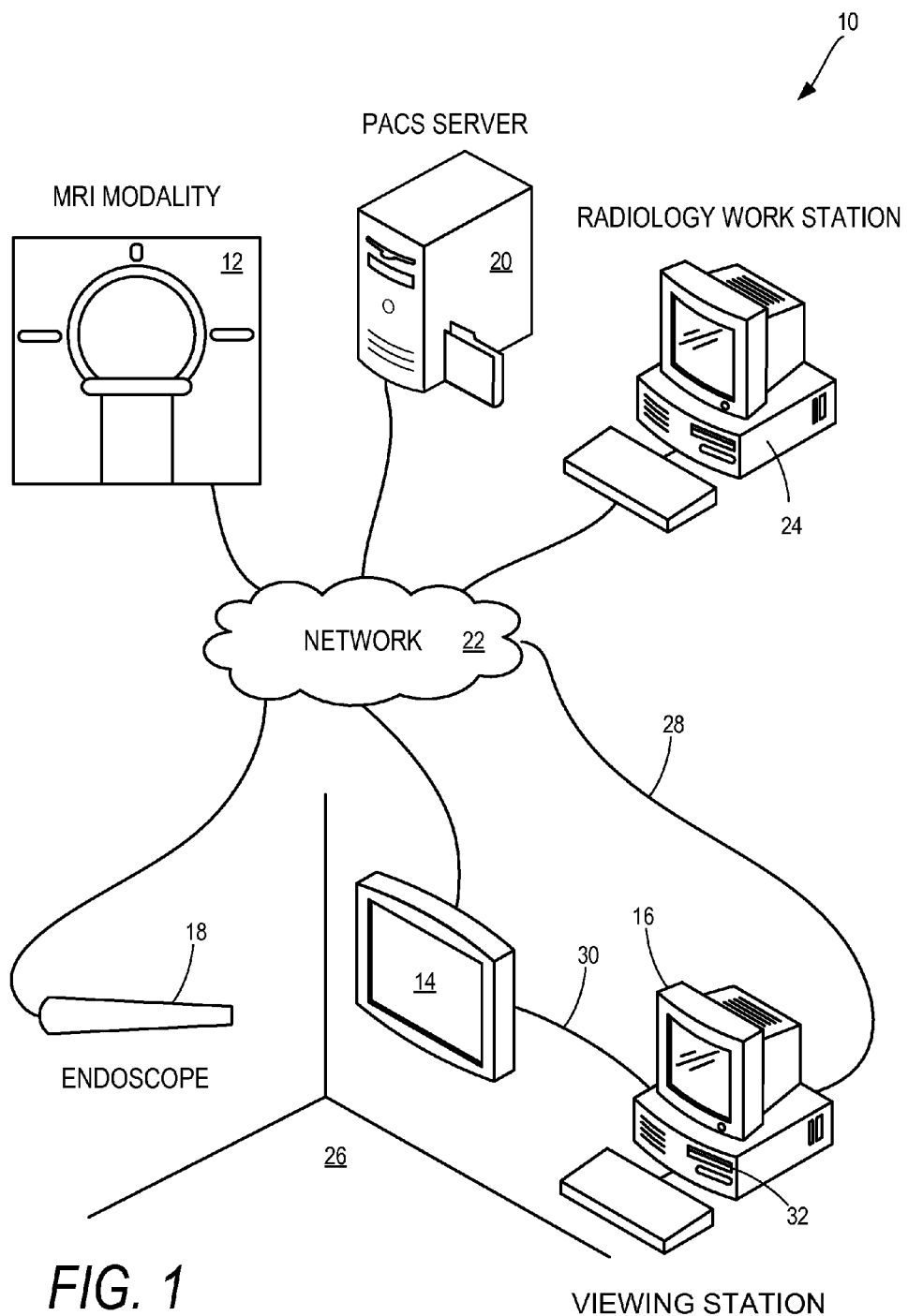
FIG. 1 shows an illustrative embodiment of a healthcare facility including a local viewing station for locally converting and displaying medical images.

Certain terminology is used herein for convenience only and is not to be taken as a limitation on the present invention.

Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

FIG. 1 shows an illustrative embodiment of a patient care facility 10 including a hospital operating or examination room 26, for example, where a patient is to receive medical attention. As shown, the patient care facility 10 includes at least one medical modality, shown as a magnetic resonance imaging ("MRI") device 12 in FIG. 1, that captures medical images associated with the patient, a display device 14 for viewing the medical image, and a computer terminal 16 in communication with the display device 14 to cause the medical image to be displayed on the display device 14.

The modality shown in FIG. 1 is a MRI device 12, but the modality can include any device capable of capturing information about the patient, possibly for diagnostic purposes. Other examples of the modality include x-ray and ultrasound machines, electronic weight scales, EKG's and any other device used to examine a patient during the provision of medical care that can collect electronic data about the patient during such an examination. An endoscope 18 is also shown in the patient care facility 10 as another example of a modality.

The display device 14 can be any video, audio, or any other suitable presentation device for offering playback of the medical images captured by the modality 12. Although the term "medical image" is used to describe the content displayed by the display 14, it is to be understood that the medical image can be any type of data collected and recorded by the MRI 12, the endoscope 18, or any other type of modality and relating to a patient. Thus, the medical image encompasses not only visible pictorial images such as x-rays, but also encompasses audio tracks such as that recorded during an ultrasound, for example. Accordingly, the display 14 can be an audio playback device, video playback device, waveform playback device, or a combination thereof. However, for the sake of brevity, the embodiments will be described below as displaying a visible medical image.

The embodiment of the patient care facility 10 shown in FIG. 1 also includes an enterprise storage solution for storing the medical images electronically. The enterprise storage solution can be a server connected to other terminals via a local area network ("LAN"), a wide area network ("WAN") such as the Internet, or a combination thereof. For the specific example described below, the enterprise network storage solution is a picture archiving and communication systems ("PACS") server 20, that stores medical images in an electronic format that is compliant with a medical imaging standard such as the Digital Imaging and Communications in Medicine ("DICOM") standard, although any other medical image standard is also within the scope of the present technology. The PACs server 20 offers a centralized and network-connected storage location where the medical files can be stored and retrieved by different authorized users over the network 22.

A radiology workstation 24 can also optionally be provided to the patient care facility 10. The radiology workstation 24 can be programmed with proprietary medical viewers that are operable to present the medical images in their proprietary format to the user. Further, the radiology workstation has the required authorization to store medical images in the PACS server 20. Analogous to the description of medical images above, the phrase "medical image viewer" is used generally herein to refer to any computer-executable instructions that, when executed, can play back or otherwise display or present the medical images to an observer. For medical images that are audio tracks, the medical image viewer can play the audio tracks to audibly present them to a listener. Similarly, for medical images that are visible images such as an x-ray, the medical image viewer can visibly display the image using a computer monitor, projector, the display 14, and so on.

The computer terminal 16 shown in FIG. 1 is connected to the network 22 via a communication channel 28 such as an Ethernet cable, wireless signal, or the like. The computer terminal 16 can be locally connected to the display 14, such as by a LAN embodiment of the network 22, optionally directly connected such as by a HDMI cable or other direct communication channel 30 extending between the computer terminal 16 and the display 14, or a combination thereof. The computer terminal 16 can optionally be disposed within the operating or examination room 26, or an adjacent or nearby room where it is out of the so-called sterile field of the operating room. Medical images can be stored, at least temporarily, in a non-transitory memory, such as a hard disk drive for example, integrated within, or otherwise accessible to the computer terminal 16. Medical images can optionally be stored on a portable computer-readable medium such as a CD, USB flash drive, etc. . . . , in communication with the computer terminal 16. Such medical images accessible to the computer terminal 16 can be presented to an observer via the display 14 without requiring the medical images to first be stored on the PACS server 20 according to the method described in detail below.

Figure 2:
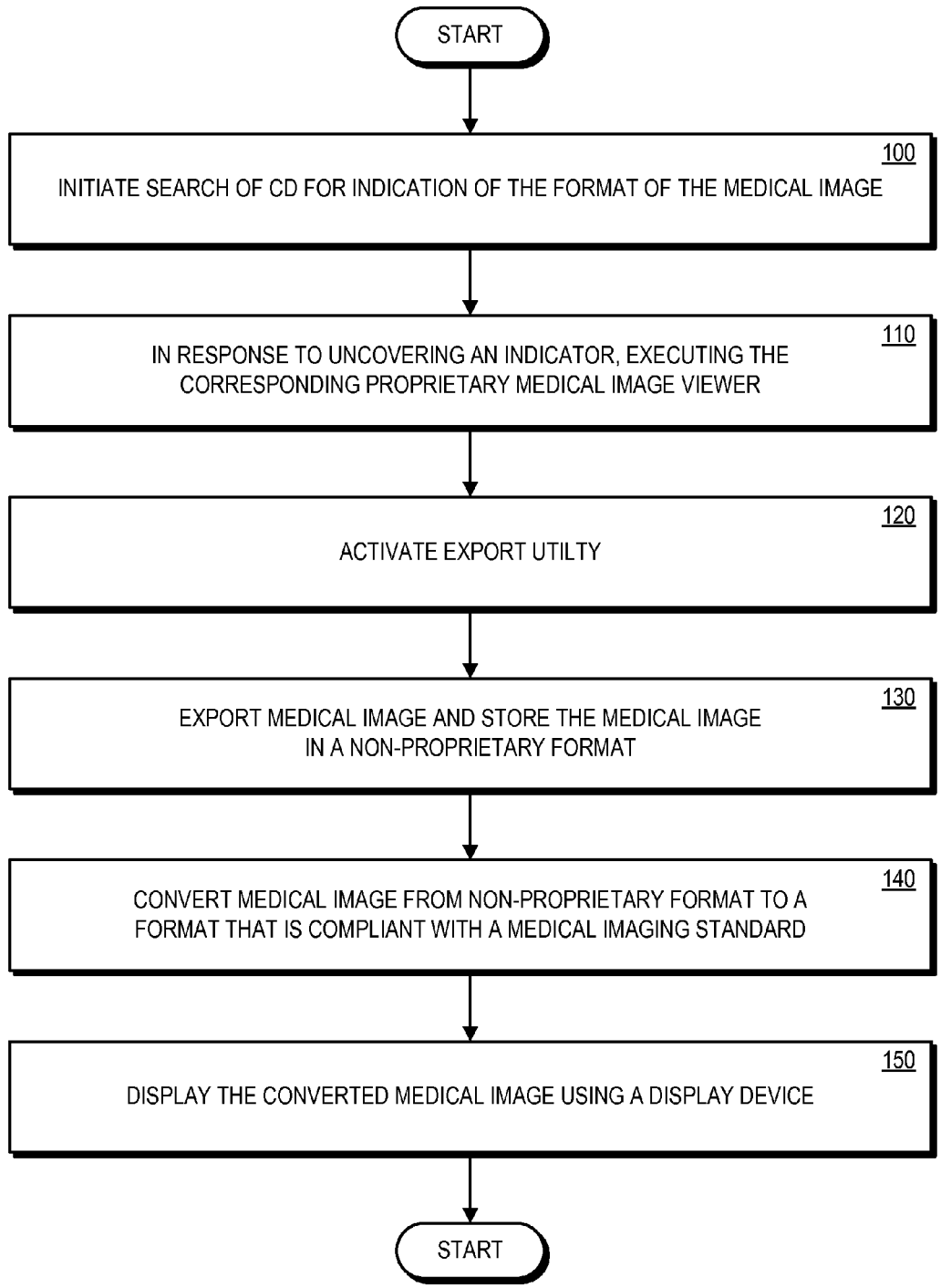
FIG. 2 shows a flow diagram schematically depicting an embodiment of a method of locally converting a medical image to be displayed from a proprietary format to a format that is compliant with a medical imaging standard.

The method described herein can optionally be performed by a computer terminal executing computer executable instructions stored in a non-transitory computer-readable medium. To describe this method, the example of a surgeon wishing to display a medical image on a CD using the display 14 during a surgical procedure will be used once again. With reference to the flow diagram of FIG. 2, the surgeon or other party in possession of a CD storing the medical image to be displayed can introduce the CD to a CD-ROM drive 32 (FIG. 1) of the computer terminal 16. An autorun function of the computer terminal 16 or an instruction from the user can result in the initiation, at step 100 of FIG. 2, of a search of the locally-delivered CD for an indicator that would allow for a determination of the format of the medical image to be displayed.

The indicator can be any information that would allow for at least an assumption, and optionally an affirmative decision, to be made about the format of the medical image, and accordingly, whether the medical image is in a proprietary format. For example, the indicator could be a file extension appended to the end of the filename for the medical image. The file extension .pdf, for example, would indicate that the medical image is an Acrobat file. According to other embodiments, the indicator can be the filename itself, or at least a portion thereof. According to such embodiments, the computer terminal 16 under the control of the computer-executable instructions, may conduct the search for a commonly-found term in the filename, optionally using wildcard placeholders as well. For example, Koninklijke Philips Electronics N.V. formats medical images in accordance with their iSite format. The computer terminal 16 may conduct the search of the CD for files including the term "isite" using the search string "*isite*.???", for example, where each "*" and "?" represent wildcard characters with "*" representing zero to many characters and "?" representing one character. If such an entry is found, it can be assumed, and optionally determined, that the CD stores a version of the proprietary viewer for viewing iSite-compatible medical images, and that at least some of the medical images are in such format. The computer terminal 16 can conduct multiple such searches based on a set of predetermined rules looking for specific indicators associated with a plurality of different vendors. The proprietary format can be any format developed by or on behalf of a specific corporate or commercial entity owning proprietary rights in software and/or hardware for capturing, storing, converting, retrieving, displaying, or any combination thereof, medical images. The proprietary rights include the right to limit others' use of the software and/or hardware for accessing such medical images in the proprietary format.

Yet other embodiments can search for an indicator that includes particular data, or a pattern of data in a file stored on the portable computer readable medium. For example, an image file in a particular proprietary format may always include the text string "ABC" in the first 16 characters of the file. A lookup table or other relationship can be referenced by the computer terminal 16 to establish that image files including "ABC" in the first 16 characters are formatted in a specific proprietary format. Searching can progress through a series of checks in any desired order in an attempt to find proprietary-format, and optionally other formats of medical images.

In response to finding an indicator of the type of medical image file format, the corresponding proprietary viewer required to view such medical images can be executed at step 110. For example, the computer terminal 16 can accomplish this by opening the file on the CD including the search term "iSite" found during a search and having the executable file extension ".exe" or "bat" or other extension indicating an executable file. Alternately, the computer terminal 16 can use a lookup table to identify the executable file for viewers compatible with the corresponding medical image format. Any suitable relationship between the executable file and the search time or medical image format identified can be used. Regardless of how it is identified, the executable file is operable to launch the proprietary viewer for viewing iSite-compatible medical images. Further, proprietary view can be executable from the CD or other portable medium, from a local memory of the terminal 16 such a hard disk drive, from a network-connected memory, or any other computer-accessible memory in communication with the terminal 16.

Many proprietary viewers stored on the portable computer-readable medium also include an export utility, which can be manually executed by users. According to an embodiment of the invention, the medical image export utility can be instructed, optionally without user intervention, by the computer terminal 16 to execute the export function for automatically decoding and saving the medical image locally, without user intervention, following selection of the medical image to be viewed. In other words, once the user selects a medical image, terminal 16 can execute the viewer, or at least the export function, to export the medical image. Exporting the medical image via the export utility allows the medical image in the proprietary format on the CD to be decoded and saved locally, such as on the hard disk of the computer terminal 16, for example, in a non-proprietary format. Examples of such a non-proprietary format include, but are not limited to JPEG, BMP, PNG, GIF, TIFF and DICOM formats. Medical images formatted as such can be observed using commonly available image viewers including some medical image viewers readily-available from several different vendors. The computer terminal 16 can select and activate the export utility at step 120, optionally in the background using a virtual monitor, and/or automatically, without user intervention following selection of the medical images to be observed. Activation of the export utility in the background results in exportation of the out of view of a user, and treating the medical image appear to be originally stored in the non-proprietary format.

If, however, at step 110 it is established that the medical image is stored on the portable computer-readable medium in a non-proprietary format other than DICOM, the medical image can optionally be saved on a computer memory such as on the hard disk of the computer terminal 16, for example, or other network-connected memory. According to such an embodiment, the medical image is converted from the non-proprietary format to a format that is compliant with a medical imaging standard, such as the DICOM medical-image standard for example, on the computer memory. The DICOM converted medical image is then transmitted to the display 14 to be displayed without requiring prior storage of the medical image in an enterprise storage solution for medical images such as the PACS server 20.

At step 130, the medical image is exported from the CD and stored, using the medical image export utility, in a non-proprietary format on the hard disk drive of the computer terminal 16 or other computer memory accessible to the computer terminal 16. Once stored in the non-proprietary format, the medical image can be converted, if required, from the non-proprietary format into the DICOM format or another format that is compliant with a medical imaging standard that has been adopted as a medical imaging standard to facilitate standardized transmission of medical images between patient care facilities at step 140 using any desired converter. The medical image in the DICOM or other medical imaging standard format is transmitted by the terminal 26 to be displayed using the display 14 at step 150. In this manner, the medical image can be converted and displayed via the display 14 locally relative to the terminal 16, and without requiring prior storage of the medical image in the PACS server 20. According to alternate embodiments, the medical image can be transmitted over the LAN and/or WAN to be displayed by the display 14 without being stored in the PACS server 20.

Figure 3:
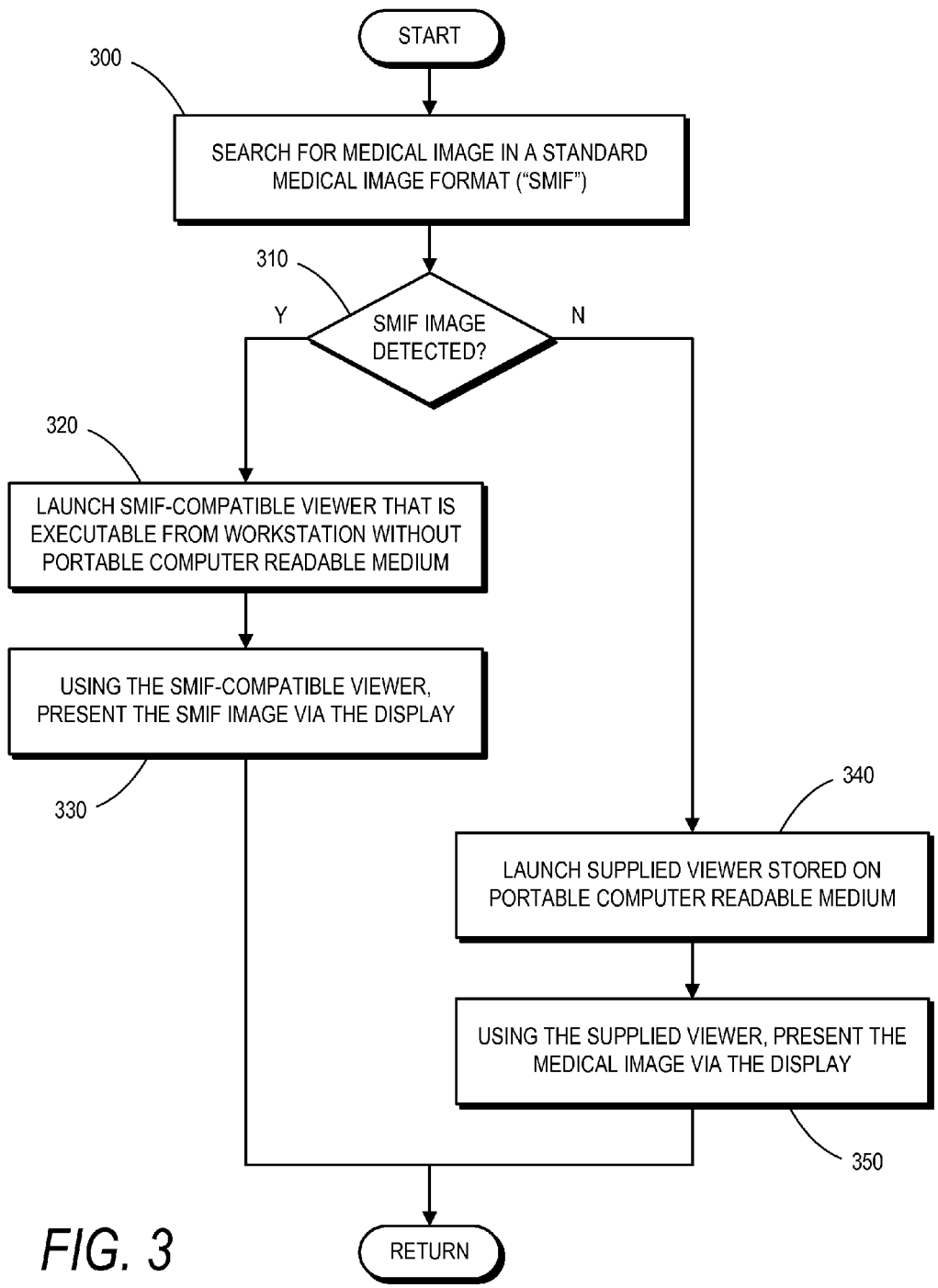
FIG. 3 shows a flow diagram schematically depicting an embodiment of a method of displaying a medical image using a medical image presentation utility selected from a plurality of available options.

An alternate embodiment of a method of presenting one or more medical images on a portable computer readable medium such as a CD is described with reference to FIG. 3. Use of the specific example of displaying an image stored on a CD is continued for describing the present embodiments. As shown at step 300, the computer terminal 16 under the control of computer executable instructions can initiate a search for an image stored in a standardized medical image format for the communication of medical images, such as the DICOM standard for example, stored on the CD. In response to a determination at step 310 that an image in the standardized medical image format is present on the CD, the computer terminal 16 launchers a viewer that is compatible with the standard medical imaging format at step 320. The standard medical image format-compatible viewer is executable by the computer terminal 16 even without the CD being present. As such, the standard medical image format-compatible viewer is stored locally by the computer terminal 16 or is otherwise accessible to the computer terminal 16 via the network 22 or source other than the CD. Using the standard medical image format-compatible viewer, the computer terminal 16 causes the medical image to be displayed via the display 14 at step 330. The displayed medical image can be displayed from the CD, from the computer terminal 16, or from any other computer-accessible memory, without being first stored in the PACS server 20.

If, however, it is determined at step 310 that a medical image in the standard medical image format is not present on the CD but a medical image in a proprietary format is, a viewer utility, which can be a proprietary viewer supplied by the manufacturer of the equipment used to create the CD, or manufacturer or source of a modality, for example, can be launched from the CD at step 340. Using the supplied viewer, the medical image formatted in a format other than the standard medical image format can be displayed via the display 14 in the format in which it was stored on the CD at step 350, and without first being converted to the standard medical image format and without previously being stored in the PACS server 20.

Figure 4A:
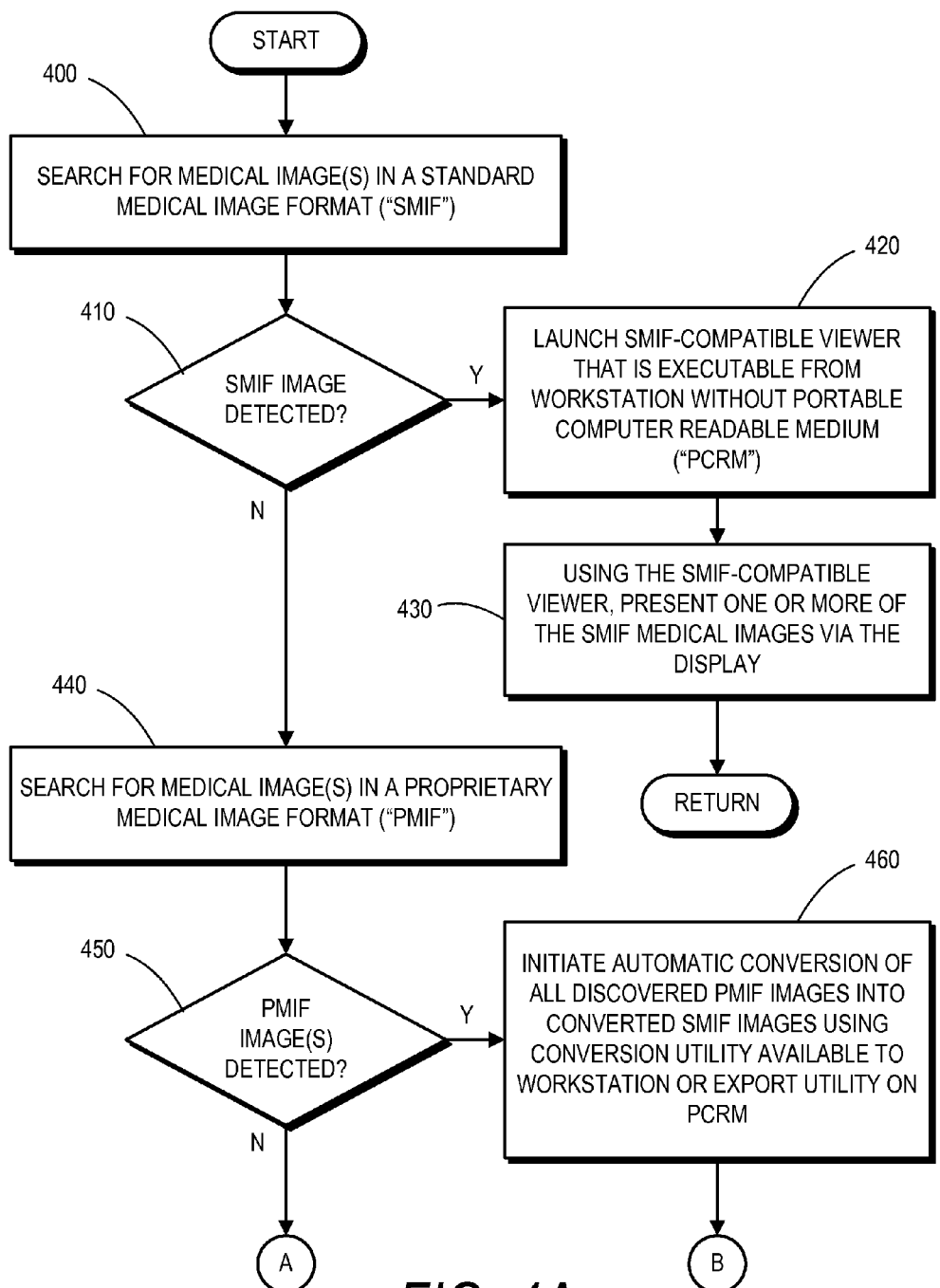
FIG. 4A shows a portion of a flow diagram illustrating an alternate embodiment of presenting a medical image delivered on a portable computer readable medium.
Figure 4B:
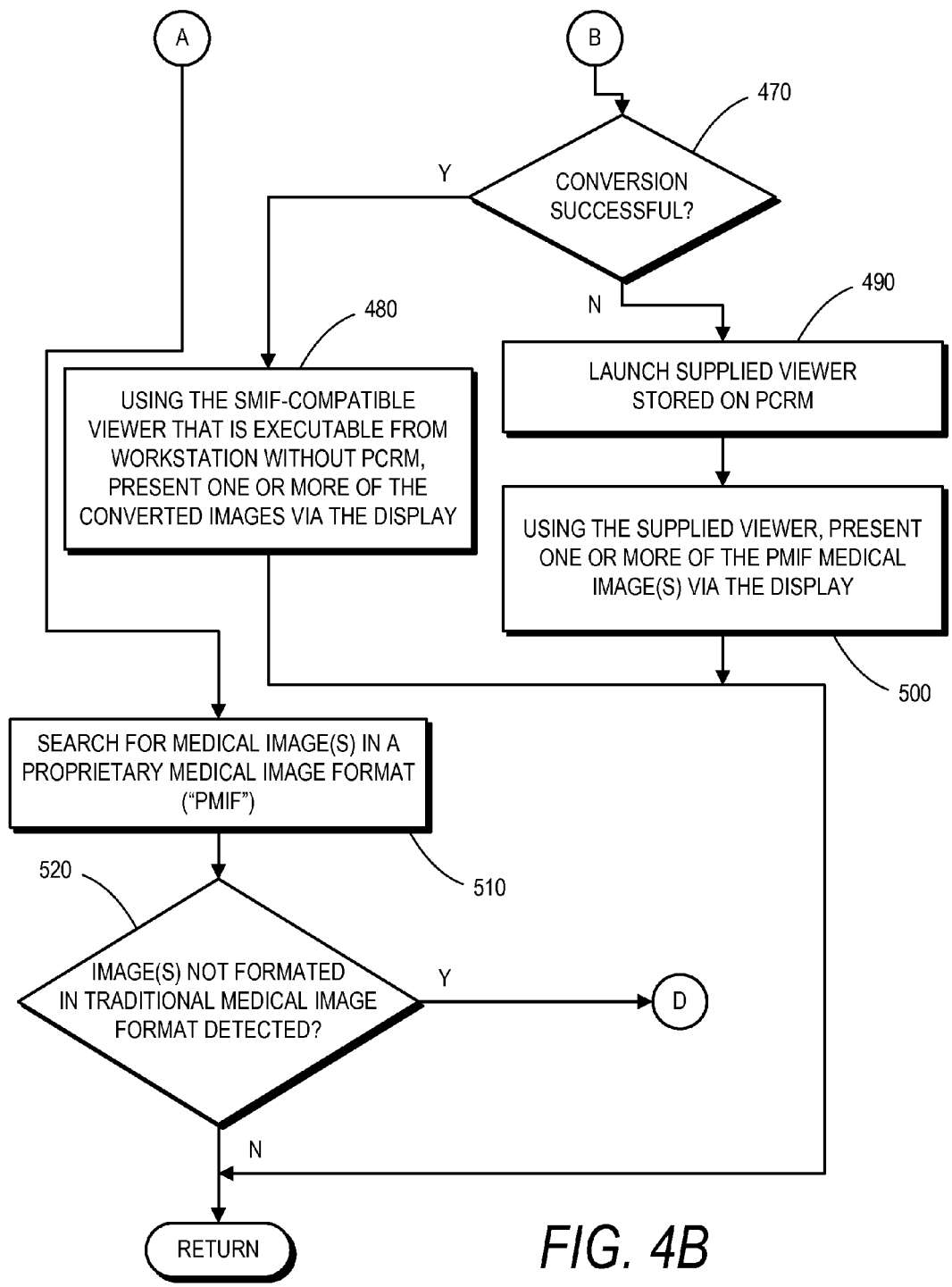
FIG. 4B shows another portion of the flow diagram used to describe a method of presenting a medical image delivered on a portable computer readable medium.
Figure 4C:
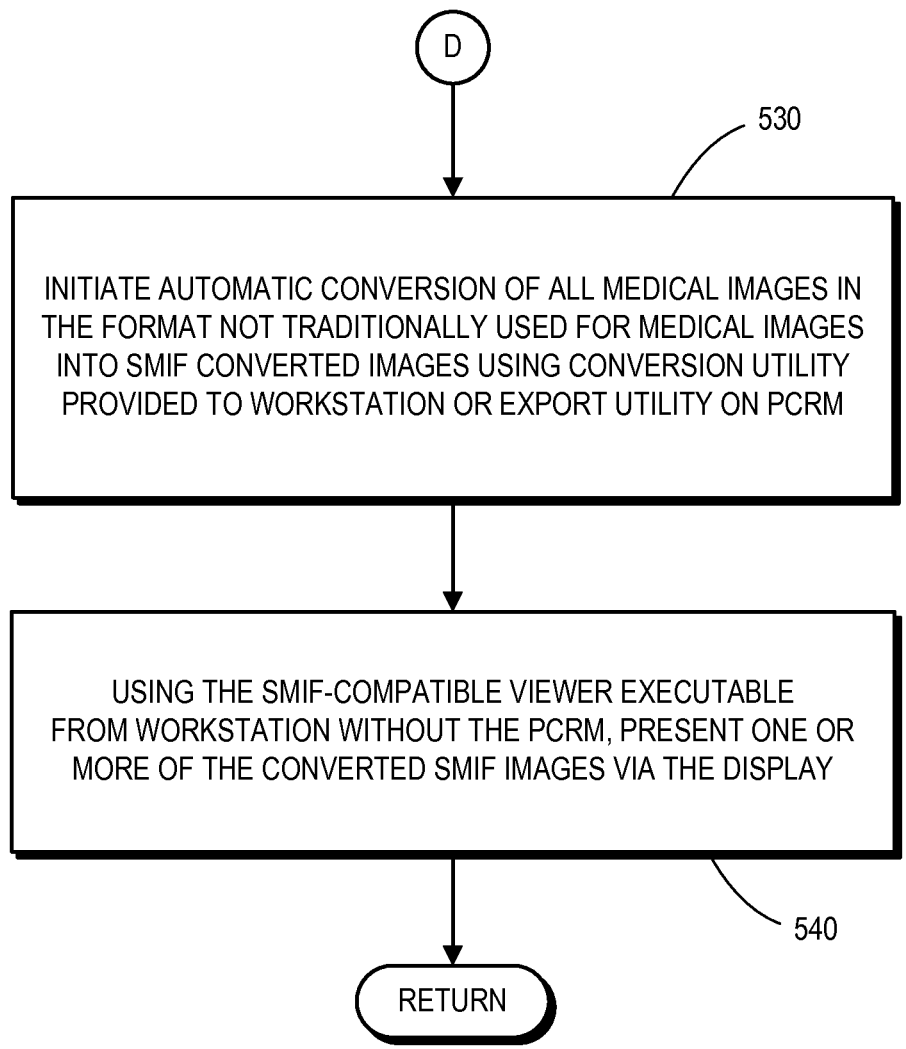
FIG. 4C shows another portion of the flow diagram used to describe a method of presenting a medical image delivered on a portable computer readable medium.

Yet another embodiment of the method of presenting a medical image can be understood with reference to FIGS. 4A-4C. Similar to the previous embodiment, a search for one or more medical images in a standard medical image format is initiated at step 400 in FIG. 4A. If it is determined at step 410 that a medical image in the standard medical image format is present on the CD, a viewer compatible with that standard medical image format is launched at step 420, and the medical image in the standard medical image format displayed at step 430.

Just as before, the viewer compatible with the standard medical image format can be an image viewer or other medical image presentation utility stored on, or otherwise executable by the computer terminal 16 without requiring the CD. Accordingly, the standard medical image format viewer local to the computer terminal 16 can be utilized to view all medical images in the standard medical image format rather than another, optionally proprietary medical image viewer present on the CD with which the user may not be familiar.

If, however, at step 410 a medical image in the standard medical image formatted is not detected, or if the desired image is not found or selected, or if a proprietary image is found in addition to the standardized image, the search is expanded to return medical images in a proprietary medical image format at step 440. The proprietary medical image format may be a format adopted by a manufacturer of computer equipment used to create the CD with the medical images, for example. If an image in the proprietary medical image format is detected at step 450, automatic conversion of all such discovered images into a standard medical image format can be initiated at step 460. This conversion can be accomplished by a conversion utility that is on the computer terminal's hard drive, or other computer memory that is accessible to the computer terminal 16 other than the CD. According to alternative embodiments, the conversion utility can be included on the CD, optionally forming part of an export utility or viewer utility stored on the CD.

The conversion of medical images can be automatic. Conversion of all of the medical images into the standard medical image format is said to be automatic in that user intervention is not required once the conversion process is initiated. Initiation can occur automatically upon detection of a proprietary or other image, or upon selection of a proprietary medical image, for example. Rather than being required to initiate conversion of each medical image on the CD manually, the conversion process can optionally automatically progress to subsequent medical images without user intervention. Thus, a 300 slice CT scan, for example, requiring the user to manually initiate conversion of the image representing each slice would be time consuming. In contrast, the automatic conversion of all images on the CD drastically reduces the time required to complete the conversion process. Alternately, users can select a plurality of images to be converted and/or viewed & conversion of the selected images can progress automatically upon initiation of the conversion process.

At step 470 it is determined whether the conversion of the medical images into the standard medical image format was successfully completed. If so, at step 480, the standard medical image format compatible viewer is launched by the computer terminal 16. Just as before, the standard medical image format-compatible viewer launched at step 480 is a local viewer rather than a similarly-compatible viewer stored on the CD to give the user the ability to use a familiar user interface.

If conversion of the medical images into the standard medical image format is unsuccessful or otherwise incomplete as determined at step 470, a viewer compatible with the proprietary medical image standard stored on the CD is launched at step 490. This viewer is used to display or otherwise present one or more of the medical images in the proprietary medical image format via the display 14 at step 500.

If there are no medical images in the standard medical image format or proprietary medical image format on the CD, the search is again expanded at step 510 to encompass any medical images in a format other than those traditionally used for medical images. Examples of such formats include JPEG and BMP formatted images. If at step 520 it is again determined that no such images are present on the CD, the method is terminated. However, if it is determined at step 520 that such images are present, automatic conversion of selected, and optionally all of such medical images into the standard medical image format is initiated at step 530 in FIG. 4C. Just as for the conversion of all medical images in the proprietary medical image format, automatic conversion of all such images does not require user intervention to initiate conversion of each individual medical image once the conversion process has been initiated. Following conversion of the medical images into the standard medical image format, the locally available standard medical image format compatible viewer is used to display or otherwise present the converted medical images via the display 14 at step 540.

By converting the medical images on the CD from various original formats into the standard medical image format, the user of the computer terminal 16 can control the display or other presentation of the medical images using a common standard medical image format viewer, regardless of the format of the medical images on the CD.

For each of the embodiments described herein, the medical images to be displayed or otherwise presented via the display 14 can be stored, at least temporarily, locally relative to the computer terminal 16, and displayed from this local storage location. For example, the medical images to be displayed can be copied, moved or otherwise exported to the hard disk drive of the computer terminal 16, from where the medical images can be transmitted to be displayed or otherwise presented via the display 14. This can optionally apply to any of the medical images to be displayed or otherwise presented via the display 14. The medical images in the proprietary format, standard medical image format, and formats other than traditional formats for medical images.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method of converting a medical image used in a network at a patient care facility, the network comprising an enterprise network storage solution where medical images stored in a standardized medical imaging format are to be retrieved over the network, the method comprising:
    with a computer system, searching a portable computer-readable medium for an indication that the medical image is stored in a proprietary format on a portable computer-readable medium;
    identifying, with the computer system, the proprietary format of the medical image based on the indication;
    converting the medical image obtained from the portable computer-readable medium in the proprietary format into a format that is compliant with a standardized medical-imaging format; and
    transmitting the medical image in the format that is compliant with the standardized medical-imaging format to be: (i) subsequently displayed by a display device without requiring prior storage of the medical image in an enterprise storage solution for medical images, and/or (ii) stored in the enterprise storage solution.

2. The method of converting the medical image of claim 1, wherein the standardized medical image format is a DICOM-compliant format in which the medical image is standardized for transmission between patient care facilities.

3. The method of converting the medical image of claim 1, wherein said searching the portable computer-readable medium comprises evaluating at least one of a file name and a file extension for one or more characters indicative of the proprietary format.

4. The method of converting the medical image of claim 3, wherein said evaluating comprises conducting a search of the at least one of the file name and the file extension for a predetermined string of characters known to be included in the at least one of the file name and the file extension by an entity supporting use of the medical image in the proprietary format.

5. The method of converting the medical image of claim 4, wherein said search comprises:
    generating a search string to be used to conduct the search by assembling the predetermined string of characters with at least one wildcard character; and
    comparing the search string with the at least one of the file name and the file extension.

6. The method of converting the medical image of claim 1, wherein said searching the portable computer-readable medium comprises evaluating content of the medical image to determine whether the content comprises data indicative of the proprietary format.

7. The method of converting the medical image of claim 6, wherein said evaluating said content comprises searching for a predetermined string of characters within a known location of the content where the predetermined string of characters is expected to be located if the medical image is in the proprietary format.

8. The method of converting the medical image of claim 1, wherein the medical image export utility is a computer program that is operable to decode the proprietary medical image format.

9. The method of converting the medical image of claim 1, wherein the enterprise storage solution for medical images comprises a picture archiving and communication system ("PACS") that stores medical images in a standardized DICOM format.

10. The method of converting the medical image of claim 1, wherein said converting the medical image comprises:
- in response to said identifying, exporting, with a medical image export utility executing on the computer system, the medical image from the portable computer-readable medium into a non-proprietary format;
- storing, at least temporarily, the medical image in the non-proprietary format in a computer-accessible memory operatively connected to the computer system; and
- converting the medical image in the non-proprietary format to the format that is compliant with the standardized medical-imaging format.

11. The method of converting the medical image of claim 10, wherein the medical image export utility is included as a portion of a proprietary medical image viewer that is operable to display the medical image in the proprietary format.

* * * * *